US008884767B2

(12) United States Patent
Kidmose (10) Patent No.: US 8,884,767 B2
(45) Date of Patent: Nov. 11, 2014

(54) METHOD AND APPARATUS FOR ALERTING A PERSON CARRYING AN EEG ASSEMBLY (75) Inventor: Preben Kidmose, Lynge (DK)

(73) Assignee: Widex A/S, Lynge (DK)

(*) Notice: Subject to any disclaimer, the term of this patent is extended or adjusted under 35 U.S.C. 154(b) by 49 days.

(21) Appl. No.: 13/481,719

(22) Filed: May 25, 2012

(65) Prior Publication Data

US 2012/0235820 A1 Sep. 20, 2012

Related U.S. Application Data (63) Continuation-in-part of application No. PCT/EP2009/066191, filed on Dec. 2, 2009.

(51) Int. Cl.
G08B 23/00 (2006.01)
G08B 5/22 (2006.01)
A61B 5/04 (2006.01)
A61B 5/0476 (2006.01)
A61B 5/00 (2006.01)
G06F 19/00 (2011.01)

(52) U.S. Cl.
CPC .......... A61B 5/0031 (2013.01); A61B 5/0476 (2013.01); A61B 5/0006 (2013.01); G06F 19/3406 (2013.01); A61B 5/6817 (2013.01); A61B 2560/0271 (2013.01); A61B 5/6816 (2013.01)
USPC ....... 340/573.1; 340/6.1; 340/7.61; 340/7.62; 600/544; 600/545; 600/379

(58) Field of Classification Search
USPC .......................................................... 600/545
See application file for complete search history.

(56) References Cited

U.S. PATENT DOCUMENTS

| 5,686,897 | A * | 11/1997 | Loh ............................... 340/649 |
| 2006/0224067 | A1 * | 10/2006 | Giftakis et al. ............... 600/483 |
| 2006/0241725 | A1 * | 10/2006 | Libbus et al. .................. 607/60 |
| 2007/0112277 | A1 * | 5/2007 | Fischer et al. ................ 600/544 |
| 2007/0279217 | A1 * | 12/2007 | Venkatraman et al. .. 340/539.12 |
| 2008/0027348 | A1 * | 1/2008 | Harris et al. .................. 600/545 |
| 2008/0293998 | A1 * | 11/2008 | Andrews ........................ 600/25 |
| 2010/0168603 | A1 * | 7/2010 | Himes et al. .................. 600/544 |

FOREIGN PATENT DOCUMENTS

| JP | 2003-290152 A | 10/2003 |
| JP | 2007-105450 A | 4/2007 |
| JP | 2009-530608 A | 8/2009 |
| WO | 2006/066577 A1 | 6/2006 |

(Continued)

OTHER PUBLICATIONS

International Search Report for PCT/EP2009/066191 dated Oct. 12, 2010.

(Continued)

Primary Examiner — Jennifer Mehmood
Assistant Examiner — Pameshanand Mahase
(74) Attorney, Agent, or Firm — Sughrue Mion, PLLC (57) ABSTRACT A method of alerting a person using an EEG assembly (201) comprises the steps of automatically alerting said person of an incidence, manipulating an external device for establishing a wireless connection between the EEG assembly (201) and the external device (202), wirelessly transmitting from the EEG assembly (201) and to the external device (202) a data message holding information identifying the incidence that triggered the alert of the person carrying the EEG assembly, and providing information related to the incidence that triggered the alert of said person using presentation means in the external device (202). The invention also relates to an apparatus operating according to the method.

19 Claims, 5 Drawing Sheets (56) References Cited

FOREIGN PATENT DOCUMENTS

| WO | 2007/047404 | A2 | 4/2007 |
|---|---|---|---|
| WO | 2007/047667 | A2 | 4/2007 |
| WO | 2007/108900 | A1 | 9/2007 |
| WO | 2007/150003 | A2 | 12/2007 |
| WO | 2008/092133 | A2 | 7/2008 |
| WO | 2009/090110 | A1 | 7/2009 |
| WO | 2009/100654 | A1 | 8/2009 |

OTHER PUBLICATIONS

Office Action for corresponding Japanese Patent Application No. 2012-539200 dated Nov. 12, 2103, with English translation.

* cited by examiner

METHOD AND APPARATUS FOR ALERTING A PERSON CARRYING AN EEG ASSEMBLY

RELATED APPLICATIONS

The present application is a continuation-in-part of application No. PCT/EP2009/066191, filed on Dec. 2, 2009, with the European Patent Office and published as WO-A1-2011066852.

BACKGROUND OF THE INVENTION

1. Field of the Invention

The present invention relates to a method for alerting a person carrying an EEG assembly. More specifically the invention relates to a method for alerting a person carrying an EEG assembly for warning of a specific biological incidence, such as a hypoglycemic attack. Moreover the invention relates to an apparatus for alerting a person carrying an EEG assembly for warning of a specific biological incidence.

Hypoglycemic attacks occur as a result of a too low blood sugar concentration, which is mostly a problem for diabetics, who are treated with insulin or other blood sugar regulating medical drugs. Others at risk include those having a genetic predisposition to having a low blood sugar. The attacks can be highly severe and often entail unconsciousness. The risk of an attack therefore often limits the possible activities of the people concerned, which furthermore decreases their quality of life. Attacks can be prevented in a simple way, e.g. by consuming appropriate food when glucose values become critically low. The problem is however that many in the risk group cannot by themselves sense when their blood sugar concentration reaches a critically low level with risk of an attack, a phenomenon known as hypoglycemic unawareness. The number of people in the risk group is approximately 10 million.

2. The Prior Art

WO-A1-2006066577 discloses an apparatus for prediction and warning of hypoglycemic attacks where an implanted unit only operates as an interface unit with a low power draw, which gathers EEG signals from one or more electrodes and transmits them wirelessly through the skin to an external unit. The external unit contains the more power demanding components including the signal processing unit and the alarm signal giver. In this case the alarm may be an acoustic signal.

WO-A1-2006066577 further discloses an apparatus for prediction and warning of hypoglycemic attacks where an implanted unit contains both signal processor, alarm giver, a rechargeable battery that is charged wirelessly through the skin by an external unit and a wireless communication circuit that allows the implanted unit to transfer data to the external unit or one or more substituting external units.

WO-A2-2007047667 discloses an apparatus containing a bioelectric measurement system, a remote monitoring system and mobile devices. The bioelectric measurement system is utilized in connection with a patient undergoing medical surveillance to measure bioelectric signal patterns associated with EEG and EMG readings. The remote monitoring system and the mobile devices are configured to receive transmissions of bioelectric related data from the bioelectric measurement system. If an emergency characteristic is detected the remote monitoring system may be directed to transmit the appropriate data and/or predefined notification alarms and messages to a medically enabled mobile device.

WO-A2-2008092133 discloses a system for monitoring a subject and its susceptibility for having a seizure. The system contains an implanted assembly and an external assembly. The external assembly may be used to provide a warning instruction. The output from the external assembly may be visual, audio, tactile (e.g. vibratory), or some combination thereof. The disclosed systems can also include an alert that is configured to indicate that there is a communication error between the implanted assembly and the external assembly. The alert can be disposed either in the internal assembly or in the external assembly. The alert can be a visible alert, an audible alert, a tactile alert, or any combination thereof. The components of the external assembly may be integrated within a housing of a typical consumer electronics device such as an MP3 player or cellular phone. The radio-frequency used to transfer data between the implantable assembly and the external assembly is at a frequency typically between 13.56 MHz and 10 Ghz.

WO-A2-2007150003 discloses a system for ambulatory, long term monitoring of a physiological signal from a patient. At least part of the system may be implanted within the patient. Brain activity signals are sampled from the patient with an externally powered leadless implanted device and transmitted to a handheld patient communication device for further processing. The external device will typically include a user interface. The user interface may be used to provide a warning signal when the implanted device is out of communication range.

When operating an EEG assembly without an external device there is not a ready means for visual presentation of relevant information.

If operating an EEG assembly with an external device connected by a wireless connection there is a risk of periods of down-time where the system is unable to alert the user.

A particular problem in an EEG assembly that relies on wireless communication is that the maintenance of a wireless connection is often relatively power consuming.

It is therefore a feature of the present invention to overcome at least these drawbacks and provide a reliable and user friendly method for alerting a user of an EEG assembly.

It is another feature of the present invention to provide an apparatus adapted for reliable and user friendly alerting of a user of an EEG assembly.

SUMMARY OF THE INVENTION

The invention, in a first aspect, provides a method of alerting a person carrying an EEG assembly about a predetermined incidence using EEG analysis, comprising the steps of fitting an EEG assembly on the person, the EEG assembly including at least one electrode adapted for detecting EEG signals from the person, signal processing means for analyzing the EEG signals for establishing a predetermined incidence in said person, alert means for alerting said person, and first link means, wherein said EEG assembly has no implanted parts, providing an external device, the external device including presentation means adapted for providing information to said person, and second link means for establishing a wireless connection with the first link means, wherein the first link means and the second link means use inductive short range communication, alerting said person about the established incidence by said alert means, manipulating the external device to activate the wireless connection between the EEG assembly and the external device, wherein the manipulation of the external device for activating the wireless connection comprises positioning the external device close to the EEG assembly, such that the distance is less than around 5 centimeters, transmitting from the EEG assembly and to the external device a data message holding information about the incidence, and providing information about the incidence using said presentation means.

This provides a method of alerting a person carrying an EEG assembly that does not suffer from the drawbacks of the prior art.

The invention, in a second aspect, provides an apparatus for alerting a person about a predetermined incidence using EEG analysis, comprising an EEG assembly including an electrode adapted for detecting EEG signals, EEG signal processing means adapted for analyzing the EEG signals for establishing a predetermined incidence, alert means adapted for alerting said person and first link means, and an external device including presentation means adapted for providing information about the incidence and second link means adapted for establishing a wireless connection with the first link means when the distance between the EEG assembly and the external device is less than around 5 centimeters, wherein the first link means is adapted for transmitting a data message in response to a request from the external device, said data message holding information establishing a predetermined incidence in said person, wherein the first link means and the second link means are adapted for near field magnetic communication and for operation in accordance with the NFC standard.

Further advantageous features appear from the dependent claims.

Still other features of the present invention will become apparent to those skilled in the art from the following description wherein the invention will be explained in greater detail.

BRIEF DESCRIPTION OF THE DRAWINGS

By way of example, there is shown and described a preferred embodiment of this invention. As will be realized, the invention is capable of other different embodiments, and its several details are capable of modification in various, obvious aspects all without departing from the invention. Accordingly, the drawings and descriptions will be regarded as illustrative in nature and not as restrictive. In the drawings.

DETAILED DESCRIPTION

In the present context an incidence capable of triggering an automatic alert of a person carrying an EEG assembly may be identification or prediction of a specific biological incidence in said person or of a technical malfunction in the EEG assembly. One example of a biological incidence is a hypoglycemic attack.

Figure 1:
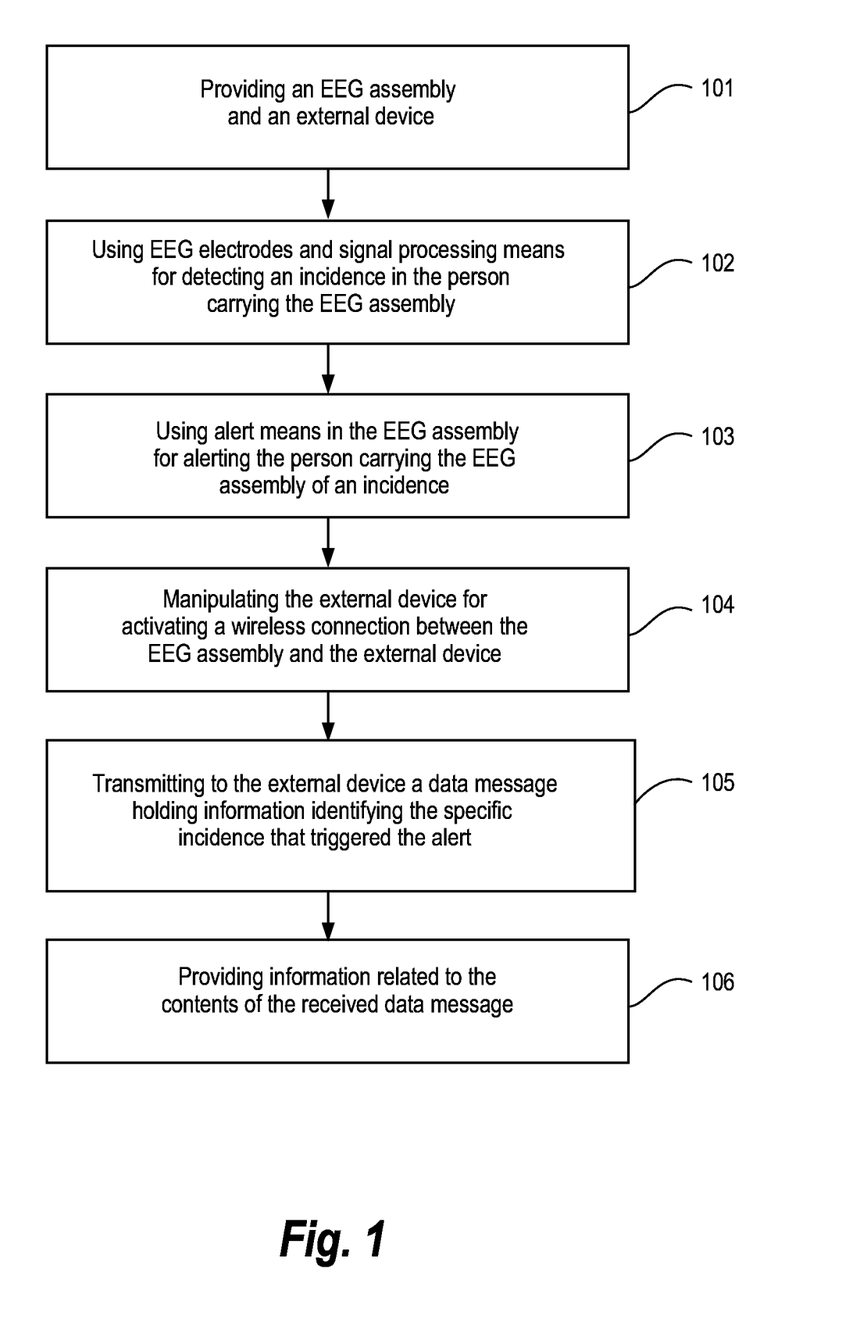
FIG. 1 illustrates a flow diagram illustrating a method of alerting a person carrying an EEG assembly according to a first method embodiment of the invention.

Reference is first made to FIG. 1, which illustrates a flow diagram of a method of alerting a person carrying an EEG assembly according to a first method embodiment of the invention. In a first step 101 an EEG assembly and an external device is provided. In a second step 102 EEG electrodes and corresponding signal processing means are used for detecting an incidence in the person carrying the EEG assembly. In a third step 103 alert means in the EEG assembly automatically alerts the person carrying the EEG assembly of an incidence. In a fourth step 104 the external device is manipulated for establishing a wireless connection between the EEG assembly and the external device. In a fifth step 105 the wireless connection is used for transmitting a data message, holding information identifying the incidence that triggered the alert, from the EEG assembly and to the external device. In the sixth and final step 106 presentation means in the first external device is used for providing information based on the contents of the received data message.

In a preferred embodiment the provided information is directed at advising the user about relieving or preventing the specific incidence that triggered the alert. In case a specific biological incidence triggered the alert the information may include instructions concerning the proper medical treatment. In case a technical error in the EEG assembly triggered the alert the information may include suggestions directed at relieving the error. In some cases a technical error can be corrected by a simple operation, e.g. a battery replacement.

In one embodiment the alert means comprises a bone anchored vibrator. In another embodiment the alert means comprises an electro-acoustical output transducer capable of sounding an audible alert. According to a preferred embodiment of the invention a simple audible beep or a short vibration is sufficient to alert the user and make him aware that he needs to establish the wireless connection between the EEG assembly and the external device in order to receive further information concerning the incidence that triggered the alert.

In a preferred embodiment the manipulation of the external device for activating the wireless connection comprises positioning the external device close to the EEG assembly. In an embodiment the distance between the EEG assembly and the external device is less than around 5 centimeters.

In one embodiment the link means, in the external device, comprises a simple push button adapted for activating the process of establishing the wireless connection.

In an embodiment activation of the link means, in the external device, triggers transmission of a series of request messages in order to establish a wireless connection with the EEG assembly. When the EEG assembly and the first external device are within the effective transmission range, the EEG assembly will reply to the request message by transmitting a data message holding information identifying the incidence that triggered the alert of the person carrying the EEG assembly.

In another embodiment activation of the link means, in the external device, triggers use of the identification and handshaking codes inherent in the NFC protocol for automatically making the EEG assembly and the first external device aware of each other when they are within proper transmission range of each other. Once identification has been performed the data message holding information identifying the incidence that triggered the alert of the person carrying the EEG assembly is transmitted to the first external device.

In one embodiment the link means, in the external device, is automatically activated when the first external device is activated. Hereby the user only needs to activate the first external device and position it within reception range of the EEG assembly in order to establish the wireless connection. This functionality may be advantageous for cognitive weak users.

In one embodiment the link means, in the external device and the EEG assembly, are adapted for near field magnetic communication. This type of wireless communication is characterized by having low electrical power consumption.

In a preferred embodiment only the link means, in the external device, generates a radio field, while the link means, in the EEG assembly, uses load modulation to transfer data. Hereby the power consumption in the EEG assembly can be kept at a minimum.

In one embodiment the link means, in the external device and the EEG assembly, are adapted for operation in accordance with the NFC standard (e.g. ISO/IEC 18092). NFC systems are high-frequency mainly inductive communication systems, which have a very short effective transmission range e.g. in the order of a few centimeters.

In one embodiment the data message only contains a number representing the specific incidence that triggered the alert of the person carrying the EEG assembly. Hereby the power consumed by the link means can be low.

In another embodiment the wireless connection is automatically de-activated by the external device once the data message has been received.

In an embodiment the alert means in the EEG assembly issues a second alert to the user when the required information has been transmitted to the external device.

In an embodiment the alert means in the EEG assembly only issues a second alert to said person once the EEG assembly has received a second data message from the external device holding information confirming that the first data message has been properly received.

In another embodiment the external device issues the second alert once the first data message has been properly received.

Preferably the second alert is easily distinguishable from the first alert. Hereby the person carrying the EEG assembly will know when the external device can again be positioned outside the effective transmission range of the wireless link means.

In an embodiment the external device only contains presentation means and link means. The presentation means comprises a visual display, menu operating means and memory means holding the information directed at relieving or preventing the specific incidence that triggered the alert. This provides a device that is inexpensive to manufacture and easy to operate.

In a further embodiment the external device presents information that requests a user input and transmits a data message to the EEG assembly holding information representing the input chosen by the user. The EEG assembly may change settings or mode of operation in response to the received data message. The data message, sent from the external device, can hold information concerning e.g.: Acknowledgement of the receipt of the data message sent from the EEG assembly, modification of the threshold for detection of an incidence, and modification of the volume of an acoustical alert or activation of data-logging.

In yet another embodiment the data message, sent from the external device and to the EEG assembly, holds information enabling an internal clock in the EEG assembly to be synchronized to a real-time clock. Hereby is provided, in the EEG assembly, a real-time clock. In one embodiment the real-time clock is used for keeping track of the occurrence of events to be stored in a data log. In an embodiment the external device is an NFC enabled mobile phone.

In another embodiment the software required in a mobile phone in order to present information directed at relieving or preventing the specific incidence that triggered the alert is implemented as a suitable Java program running on the mobile phone.

According to one embodiment said Java program is stored in the mobile phone at the same time the person is fitted with the EEG assembly.

In an embodiment, the required software is stored in the EEG assembly. This allows the EEG assembly to transmit the required software to the mobile phone. This may be done in response to a triggered alert or at any other time. The EEG assembly will initiate transmission of the software to the mobile phone after the EEG assembly and the mobile phone have become aware of each other. In a preferred embodiment this is done in accordance with the NFC standard.

In another embodiment the required software is stored on a specific network server. This allows the EEG assembly to transmit instructions requiring the mobile phone to connect to the specific network server for download of the software. Hereby any internet enabled mobile phone can be used for accessing and presenting information related to the incidence that triggered the alert of the person carrying the EEG assembly.

In yet another embodiment the EEG assembly transmits instructions requiring the mobile phone to connect to one or more mobile phones and forward information relating to the incidence that triggered the alert. Hereby is provided an advantageous method for alerting e.g. relatives and care personnel.

Figure 2:
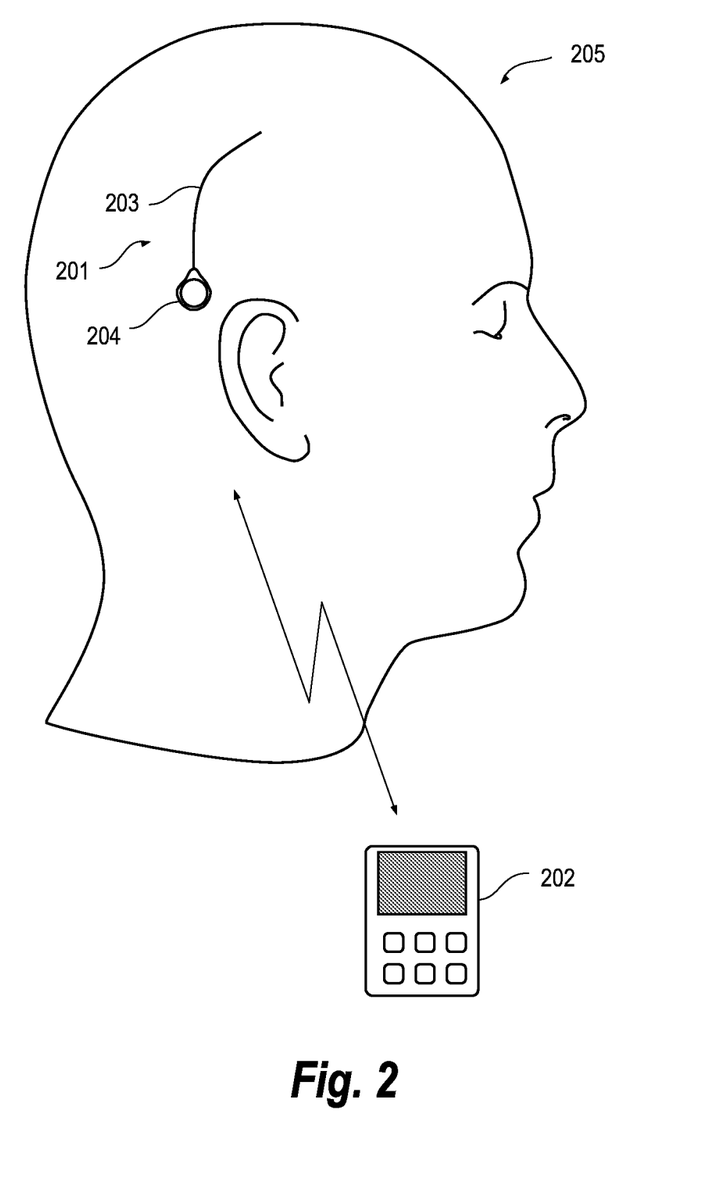
FIG. 2 illustrates highly schematically an EEG assembly and a first external device according to a first apparatus embodiment of the invention.

Reference is now made to FIG. 2, which illustrates highly schematically an apparatus for alerting a person carrying an EEG assembly adapted for warning of a specific biological incidence according to a first apparatus embodiment of the invention.

The apparatus includes an EEG assembly 201 and an external device 202. The EEG assembly 201 is configured for subcutaneous implantation behind the ear of a person 205 carrying the assembly. The EEG assembly 201 includes a first implanted subpart 203 and a second implanted subpart 204. The first subpart 203 consists of a probe having two active areas, where each active area constitutes an electrode, for contacting subcutaneous tissue in order to detect the presence of an electrical signal. The second subpart 204 includes signal processing circuitry, an alarm giver and wireless link means. According to the embodiment the signal processing circuitry is adapted for converting the signal obtained by the electrodes into digital form and analyzing the digital signal in order to identify or predict a specific incidence. If a specific incidence is identified or predicted the signal processing circuitry is adapted for automatically activating an alarm signal in order to alert the person 205 carrying the EEG assembly of the identified or predicted incidence. Further the signal processing circuitry is adapted for setting a data flag indicating that an alarm has been signaled and for storing information representing the type of incidence that triggered the alert. The wireless link means in the second subpart 204 is adapted for communication with the external device 202.

The external device 202 is adapted for establishing a wireless connection with the EEG assembly 201 and for receiving information from the EEG assembly 201 using the established wireless connection. The external device 202 also includes presentation means adapted for providing information on how to relieve or prevent a specific incidence in said person.

According to an embodiment the first implanted subpart 203 may consist of two or more probes each having two or more electrodes. Hereby the ability to identify and predict specific incidences may be improved.

In one embodiment the EEG assembly comprises a rechargeable battery.

In one embodiment the first external device comprises a standard battery and in another embodiment it comprises a standard rechargeable battery.

In one embodiment the presentation means in the first external device comprises visual display, menu operating means and memory means holding the information directed at relieving or preventing the specific incidence that triggered the alert.

Figure 3:
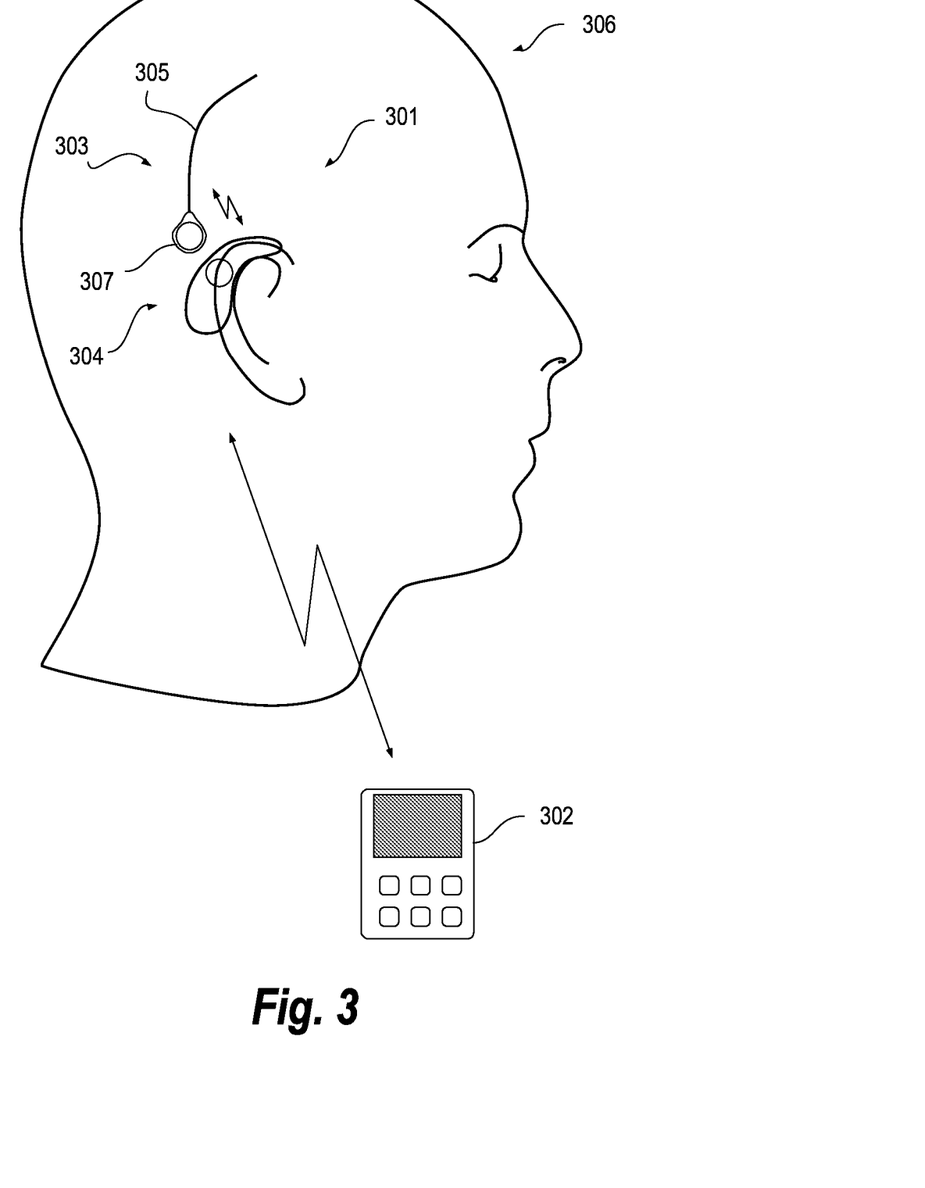
FIG. 3 illustrates highly schematically an EEG assembly and a first external device according to a second apparatus embodiment of the invention.

Reference is now made to FIG. 3, which illustrates highly schematically an apparatus for alerting a person carrying an EEG assembly adapted for warning of specific biological incidence according to a second apparatus embodiment of the invention. The apparatus consists of an EEG assembly 301 and an external device 302. The EEG assembly 301 further consists of two separate mechanical parts, an implanted part 303 that is configured for subcutaneous implantation behind the ear of a person 306 carrying the EEG assembly and a behind-the-ear part 304.

The implanted part 303 can be further divided into a first implanted subpart 305 and a second implanted subpart 307. The first implanted subpart 305 consists of a probe having two electrodes and is similar to the implanted subpart 203 described with reference to FIG. 2. The second implanted subpart 307 includes signal processing circuitry, and wireless link means. The signal processing circuitry is adapted for converting the signal obtained by the electrodes into digital form, and the wireless link means are adapted for transmitting the digital signal to the behind-the-ear part 304.

The behind-the-ear part 304 of the EEG assembly 301 includes signal processing circuitry, an alarm giver and wireless link means. The signal processing circuitry is adapted for analyzing the digital signal received from the second implanted subpart 307 in order to identify or predict a specific incidence and for activating the alarm giver if a specific incidence is identified or predicted. The wireless link means in the behind-the-ear part 304 is adapted for communication with the implanted subpart 307 in order to receive the digitized electrode signal and in addition hereto adapted for communication with the external device 302 in order to transmit data representing an identified or predicted incidence.

In an embodiment the wireless connection between the implanted part 303 and the behind-the-ear part 304 serves two purposes. The first is to transmit the digital electrode signal from the implanted part 303 and to the behind-the-ear part 304 for further analysis and processing. The second purpose is to transmit power from the behind-the-ear part 304 and to the implanted part 303. In such a configuration the implanted part 303 of the EEG assembly does not have its own source of energy, whereas the behind-the-ear part 304 is battery powered. Therefore the implanted part 303 relies on the wireless inductive power transmission from the behind-the-ear part 304.

The external device 302 comprises components similar to those described for the external device 202 with reference to FIG. 2. Consequently the external device 302 comprises link means adapted for establishing a wireless connection with the behind-the-ear part 304. Therefore according to an embodiment the wireless link means in said behind-the-ear part 304 of the EEG assembly 301 serves a third purpose in addition to the first and second purpose described above.

According to an embodiment the wireless connection between the implanted part 303 and the behind-the-ear part 304 is configured for a carrier frequency around 1 MHz, and the wireless connection between the external device 302 and the behind-the-ear part 304 is configured for a carrier frequency around 13 MHz.

According to embodiments the carrier frequency of the first connection may be in the range of 0.50 MHz to 3.0 MHz and the carrier frequency of the second connection may be in the range between 9 and 15 MHz.

According to an embodiment the wireless link means in the behind-the-ear part 304 can be adapted for wireless communication at a first and a second carrier frequency simply by switching between two capacitors having capacitance values optimized for the first and the second carrier frequency respectively.

According to an embodiment the wireless link means in the behind-the-ear part 304 comprises only one coil adapted for both of the two carrier frequencies.

Figure 4:
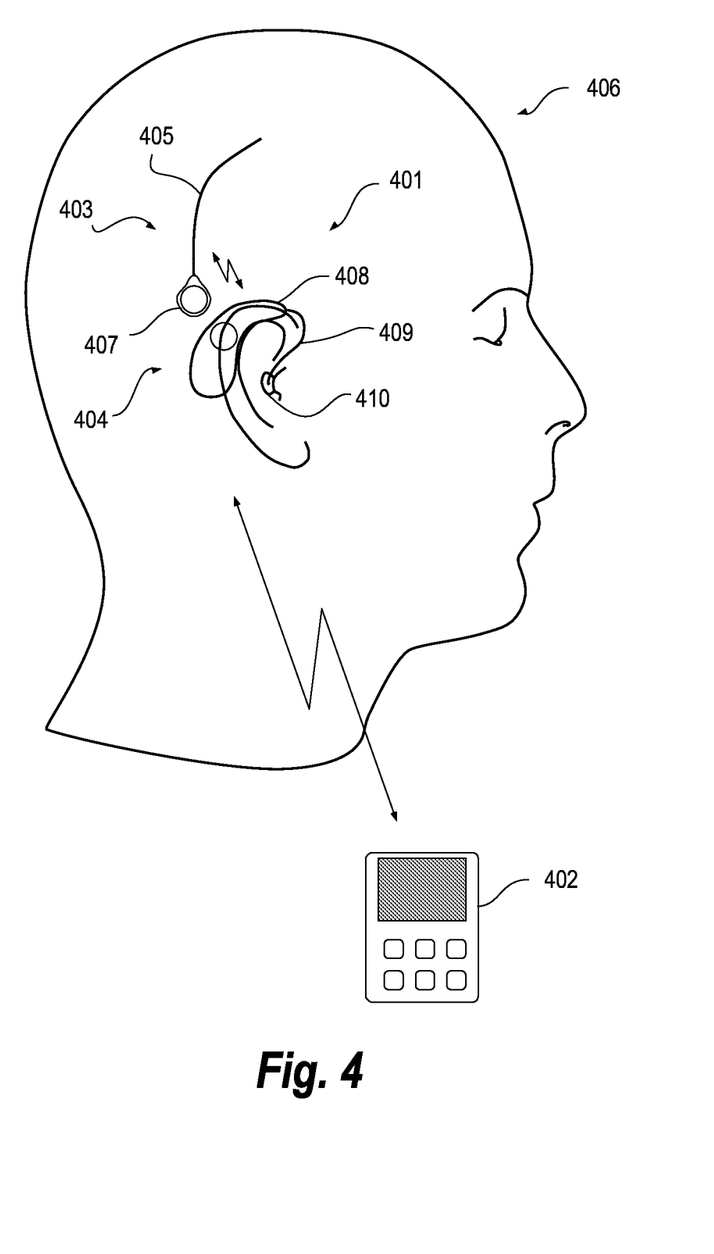
FIG. 4 illustrates highly schematically an EEG assembly and a first external device according to a third apparatus embodiment of the invention.

Reference is now made to FIG. 4, which illustrates highly schematically an apparatus for alerting a person carrying an EEG assembly for warning of specific biological incidence according to a third apparatus embodiment of the invention. The apparatus consists of an EEG assembly 401 and an external device 402. The EEG assembly 401 further consists of two separate mechanical parts, an implanted part 403 and a behind-the-ear part 404.

The implanted part 403 can be further divided into a first implanted subpart 405 and a second implanted subpart 407. The first implanted subpart 405 is similar to the implanted subparts 203 and 305 described with reference to FIG. 2 and FIG. 3 respectively. The second implanted subpart 407 is similar to the implanted subpart 204 and 307 described with reference to FIG. 2 and FIG. 3 respectively.

The behind-the-ear part 404 consists of a housing part 408, an earpiece part 410 and a connector part 409. The housing part 408 comprises signal processing circuitry and wireless link means similar to the circuitry and link means in the behind-the-ear part 304 described with reference to FIG. 3. The housing part 408 further includes an electro-acoustical alarm giver (not shown). The earpiece part 410 and connector part 409 are adapted to convey the acoustical alarm signal, from the electro-acoustical alarm giver towards the ear drum of the person 406.

In one embodiment the connector part 409 is a sound tube that conveys the acoustical alarm signal from the electro-acoustical output transducer, positioned in the housing part 408, towards the eardrum, and the earpiece part 410 is adapted to position the connector part 409 in the ear canal.

In an alternative embodiment the earpiece part 410 is adapted to position the electro-acoustical output transducer in the ear canal, and the connector part 409 is adapted to provide the electrical connection between the signal processing circuitry in the housing part 408 and the output transducer in the earpiece part 410.

The external device 402 comprises components similar to those described with reference to FIG. 2 and FIG. 3.

Figure 5:
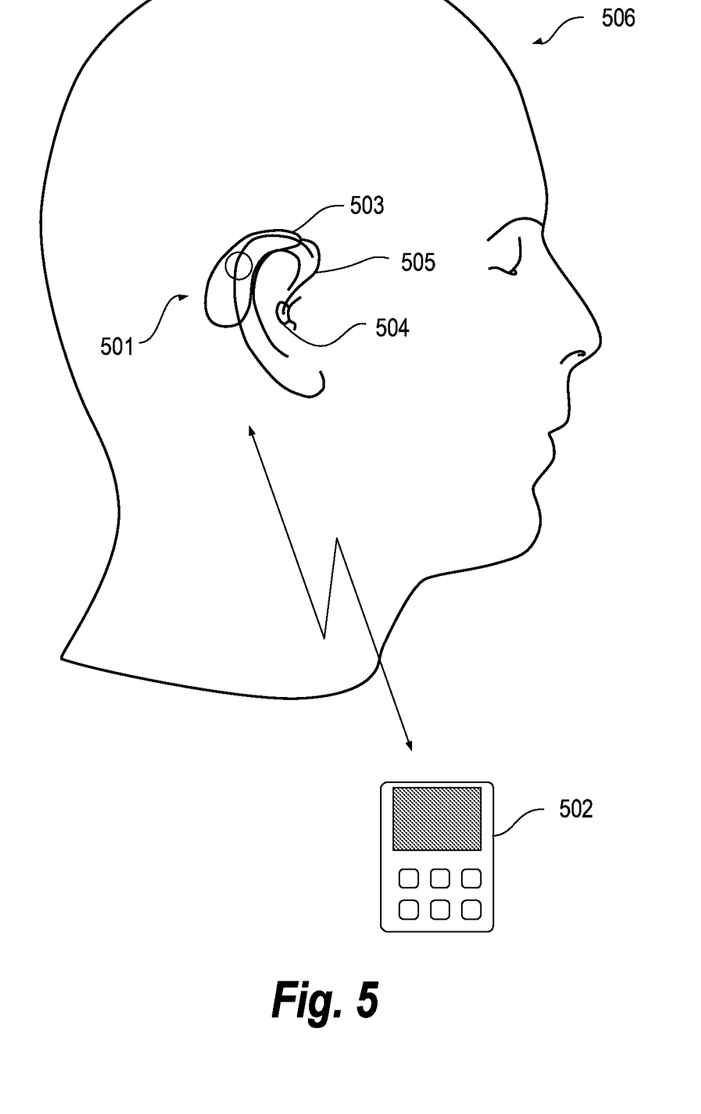
FIG. 5 illustrates highly schematically an EEG assembly and a first external device according to a fourth apparatus embodiment of the invention.

Reference is now made to FIG. 5, which illustrates highly schematically an apparatus for alerting a person carrying an EEG assembly for warning of specific biological incidence according to a third apparatus embodiment of the invention. The apparatus consists of an EEG assembly 501 and an external device 502.

The EEG assembly 501 comprises three external parts: a housing part 503, an earpiece part 504 and a connector part 505. The earpiece part 504 comprises a shell with two electrodes (not shown) adapted for measuring brain wave signals, wherein the contours of the outer surface of the earpiece shell and the electrodes are individually matched to at least part of the ear canal and the concha of the ear of the person 506 carrying the EEG assembly. The connector part 505 provides the electrical connection between said electrodes and the housing part 503. The housing part 503 comprises signal processing circuitry, an acoustical alarm giver and wireless link means. The signal processing circuitry functions similar to the circuitry described with reference to e.g. the implanted subpart 204 of FIG. 2. The earpiece part 504 and connector part 505 are further adapted to convey the acoustical alarm signal, from the acoustical alarm giver towards the ear drum of the person 506.

The external device 502 comprises components similar to those described with reference to FIG. 2, FIG. 3 and FIG. 4. Hereby a system without implanted parts is provided.

In an embodiment the earpiece part 504 comprises signal processing circuitry adapted for converting the signal obtained by the electrodes into digital form, the connector part 505 is adapted for transmitting the digital signal to the housing part 503 and the signal processing circuitry in the housing part 503 is adapted for receiving the digitized electrode signal.

Other modifications and variations of the structures and procedures will be evident to those skilled in the art.

I claim:

1. A method of alerting a person about a predetermined incidence using EEG analysis, comprising the steps of:
    fitting an EEG assembly on the person, the EEG assembly including first and second parts, said first part including at least one electrode adapted for detecting EEG signals from the person, said second part including a wireless communication component for establishing a first wireless link with said first part and a signal processor for analyzing the EEG signals for establishing a predetermined incidence in said person, one of said first and second parts including an alert component configured to alert said person,
    transmitting power from the second part to the first part via said first wireless link;
    providing an external device, the external device including a presentation component configured to provide information to said person, and a wireless communication component configured to establish a second wireless link with the EEG assembly,
    alerting said person about the established incidence by said alert component,
    establishing said second wireless link,
    wirelessly transmitting from the EEG assembly and to the external device a data message holding information about the incidence, and
    providing information about the incidence using said presentation means component.

2. The method according to claim 1, comprising a step of incorporating into the EEG assembly a signal processing component configured to detect a technical malfunction in the EEG assembly.

3. The method according to claim 2, comprising a step of alerting said person about a technical malfunction in the EEG assembly.

4. The method according to claim 1, wherein said alert component uses a bone anchored vibrator.

5. The method according to claim 1, wherein said alert component uses an electro-acoustical transducer.

6. The method according to claim 1, wherein the second wireless link operates in accordance with the NFC standard.

7. The method according to claim 1, wherein the external device is a mobile phone.

8. The method according to claim 1, wherein the step of fitting the EEG assembly comprises
    fitting said first part at least partly in the ear canal of said person, said first part comprising the electrode, electrode signal processing circuitry adapted for converting the signal obtained by the electrode into digital form and the alert component, the alert component being configured to produce an acoustical alert and conveying the acoustical alert by a sound channel towards the ear drum of said person,
    fitting said second part to be carried behind the ear of said person, said second part comprising the EEG signal processor and said wireless communication component for establishing said first link, and
    fitting a connector part adapted for operationally connecting the EEG signal processor with the alert component and with the electrode signal processing circuitry.

9. The method according to claim 1, wherein the step of fitting the EEG assembly comprises
    fitting said first part at least partly in the ear canal of said person, said first part comprising the electrode, electrode signal processing circuitry adapted for converting the signal obtained by the electrode into digital form and a sound channel adapted for conveying an acoustical alert towards the ear drum of said person,
    fitting said second part to be carried behind the ear of said person, said second part comprising the EEG signal processor, a further wireless communication component for establishing said second wireless link and the alert component, the alert component being configured to produce the acoustical alert, and
    fitting a connector part, wherein the connector is adapted for operationally connecting the EEG signal processor with the electrode signal processing circuitry and wherein the connector comprises a sound tube for conveying the acoustical alert from the second part to the first part.

10. The method according to claim 1, wherein said first part is implanted subcutaneously.

11. The method according to claim 1, wherein said second wireless link uses inductive short range communication.

12. The method according to claim 1, wherein said step of establishing said second wireless link comprises manipulating said external device.

13. An apparatus for alerting a person about a predetermined incidence using EEG analysis comprising
    an EEG assembly including first and second parts, said first part including an electrode adapted for detecting EEG signals and a wireless communication component for establishing a first wireless link with said second part, said second part including an EEG signal processor for analyzing the EEG signals for establishing a predetermined incidence, and further including a power transmission component for transmitting power to said first part via said first wireless link, one of said first and second parts including an alert component configured to alert said person, and
    an external device including a presentation component adapted for providing information about the incidence and for communicating wirelessly with said EEG assembly via a second wireless link,
    wherein the EEG assembly is configured to transmit a data message via said second wireless link in response to a request from the external device, said data message including information about the occurrence of a predetermined incidence in said person.

14. The apparatus according to claim 13 wherein said external device comprises a user-operable activation component to activate establishment of the second wireless link.

15. The apparatus according to claim 13, wherein the first part is adapted to be implanted subcutaneously outside the skull of said person, said first part comprising the electrode and the alert component, and wherein said second part is adapted to be carried behind the ear of said person, said second part comprising the EEG signal processor.

16. The apparatus according to claim 13, wherein
said first part is adapted to be worn at least partly in the ear canal of said person, said first part comprising the electrode, electrode signal processing circuitry adapted for converting the signal obtained by the electrode into digital form and the alert component, the alert component being adapted for producing an acoustical alert and conveying the acoustical alert by a sound channel towards the ear drum of said person,
said second part is adapted to be carried behind the ear of said person and comprising the EEG signal processor, and
said EEG assembly further comprising a connector part adapted for operationally connecting the EEG signal processor with the alert component and with the electrode signal processing circuitry.

17. The apparatus according to claim 13, wherein the EEG assembly comprises
said first part adapted to be worn at least partly in the ear canal of said person, said first part comprising the electrode, electrode signal processing circuitry adapted for converting the signal obtained by the electrode into digital form and a sound channel adapted for conveying an acoustical alert towards the ear drum of said person,
said second part adapted to be carried behind the ear of said person, said second part comprising the EEG signal processor and the alert component adapted for producing the acoustical alert, and
a connector part adapted for operationally connecting the EEG signal processor with the electrode signal processing circuitry, and wherein the connector comprises a sound tube for conveying the acoustical alert from the second part to the first part.

18. The apparatus according to claim 13, wherein said first part is implanted subcutaneously.

19. The apparatus according to claim is 13, wherein at least one of said first and second wireless links uses inductive short range communication.

* * * * *